United States Patent [19]
Pollner et al.

[11] Patent Number: 5,534,414
[45] Date of Patent: Jul. 9, 1996

[54] PROCESS FOR PREPARING CONJUGATES CONSISTING OF A SPECIFIC BINDING PARTNER AND A CARBOHYDRATE-CONTAINING PROTEIN

[75] Inventors: Reinhold Pollner; Michael Noah; Günther Nau, all of Marburg, Germany

[73] Assignee: Behringwerke Aktiengesellschaft, Marburg, Germany

[21] Appl. No.: 414,058

[22] Filed: Mar. 30, 1995

Related U.S. Application Data

[63] Continuation of Ser. No. 145,502, Nov. 4, 1993, abandoned.

[30] Foreign Application Priority Data

Nov. 6, 1992 [DE] Germany ............ 42 37 479.0

[51] Int. Cl.$^6$ ............ G01N 33/576; C12N 9/96
[52] U.S. Cl. ............ 435/794; 435/5; 435/7.93; 435/7.95; 435/188; 530/391.3; 530/391.5
[58] Field of Search ............ 435/7.93, 7.94, 435/7.95, 188, 5; 530/391.3, 391.5

[56] References Cited

U.S. PATENT DOCUMENTS

| | | |
|---|---|---|
| 4,002,532 | 1/1977 | Weltman et al. |
| 4,587,044 | 5/1986 | Miller et al. ............ 536/28 |
| 5,248,772 | 9/1993 | Siiman et al. ............ 424/649 |

FOREIGN PATENT DOCUMENTS 0209155  1/1987  European Pat. Off.

OTHER PUBLICATIONS

"Immunoassay of Endogenous Plasma Insulin In Man", Rosalyn S. Yalow et al., J. Clin. Invest., 39:1157–1175 (1960).

"Enzyme–linked immunosorbent assay (ELISA) Quantitative assay of immuno–globulin G", Eva Engvall et al., Immunochemistry, 8(9-I):871–874 (1971).

"Immunoassay Using Antigen–Enzyme Conjugates", B. K. Van Weemen et al., FEBS–Letters, 15(3):232–236 (1971).

"Enzyme–Labeling of Antibodies and Their Fragments for Enzyme Immunoassay and Immunohistochemical Staining", Eiji Ishikawa et al., Journal of Immunoassay, 4(3):209–327 (1983).

"A Sandwich Enzyme Immunoassay of Rabbit Immunoglobulin G with an Enzyme Method and a New Solid Support", Hideaki Tanimori et. al., Journal of Immunological Methods, 62:123–131 (1983).

"Preparation of Protein Conjugates via Intermolecular Disulfide Bond Formation", Te Piao King et al., Biochemistry, 17(8):1499–1506 (1978).

"Preparation of enzyme–antibody or other enzyme–macromolecule conjugates", P. Tijssen, Laboratory Techniques in Biochemistry and Molecular Biology, pp. 221–278 (1985).

"Coupling of Enzymes to Proteins With Glutaraldehyde", Stratis Avrameas, Immunochemistry, 6:43–52 (1969).

Nakane, P and Kawaoi, A., "Peroxidase–Labeled Antibody: A New Method of Conjugation." The Journal of Histochemistry and Cytochemistry, vol. 22, No. 12, pp. 1084–1091, 1974.

*Primary Examiner*—Mary E. Ceperley
*Attorney, Agent, or Firm*—Finnegan, Henderson, Farabow, Garrett & Dunner

[57] ABSTRACT

The invention relates to a process for preparing conjugates consisting of a specific binding partner and a carbohydrate-containing protein, conjugates which can be prepared by this process and their use in enzyme immunoassays.

17 Claims, No Drawings

PROCESS FOR PREPARING CONJUGATES CONSISTING OF A SPECIFIC BINDING PARTNER AND A CARBOHYDRATE-CONTAINING PROTEIN

This application is a continuation of application Ser. No. 08/145,502 filed Nov. 4, 1993, now abandoned.

The invention relates to a process for preparing conjugates consisting of a specific binding partner and a carbohydrate-containing protein, conjugates which can be prepared by this process and their use in enzyme immunoassays.

After Yalow and Berson (R. S. Yalow, S. A. Berson (1960) J. Clin. Invest. 39, 1157–1175) described the first radioimmunoassay and Engvall and Perlmann (E. Engvall, P. Perlmann (1971) Immunochemistry 8, 871–874) as well as van Weemen and Schuurs (B. K. van Weeman, A. H. W. M. Schuurs (1971) FEBS-Letters 15, 232–236) described the first enzyme immunoassays (EIA), these techniques were employed all over the world for determining a wide variety of analytes.

Immunological methods of detection are generally distinguished by exceptional specificity and sensitivity.

Nowadays, these techniques are not merely applied just in research laboratories, but have long since been introduced into routine diagnostics and analysis.

In an enzyme immunoassay for determining analytes present at low concentration, immunological binding partners, such as, for example, antigens, haptens, antibodies or derivatives or fragments of antibodies, are employed which are coupled to a labelling enzyme via a covalent bond. The coupling products, between the immunological binding partner and the labelling enzyme, which are obtained are generally termed conjugates.

Alkaline phosphatase, β-galactosidase and horseradish peroxidase are frequently used as labelling enzymes for enzyme immunoassays, with chromogenic, fluorogenic or luminescent compounds being used as substrates. In addition, other types of labelling, such as, for example, using fluorescent dyes or molecules which are capable of chemoluminescence, are known to the person skilled in the art.

Concave molded bodies, such as, for example, small tubes or depressions in the form of microtitration plates, and convex molded bodies, such as, for example, spheres, microparticles (latex particles), rods and magnetic particles, are used as the solid phase. Planar solid phases, such as, for example, test strips, are also employed. Polystyrene and other materials are frequently used as the materials for the solid phase of enzyme immunoassays.

The possible test principles of an enzyme immunoassay, the composition of sample buffers, incubation buffers and washing buffers, and the substrate/chromogen reagents, are known to the person skilled in the art.

The labelling enzyme can be coupled to the immunological binding partner using, for example, the glutaraldehyde method (one-or two-step method, S. Avrameas (1969) Immunochemistry 6, 43–52), the periodate method (P. K. Nakane and A. Kawaoi (1974) J. Histochem. Cytochem. 22, 1084–1901) or heterobifunctional conjugation methods (F. Wold (1972) Methods Enzymol. 25, 623–651) (Review article: E. Ishikawa et al. (1983) J. Immunoassay 4, 209–327). The use of heterobifunctional reagents, which as bridging agents make possible the crosslinking of the labelling enzyme and the immunological binding partner, permitted the preparation of conjugates which were substantially better characterized. In this context, it proved to be particularly advantageous that the binding affinity of the immunological component was less impaired in the heterobifunctional method than it was in the glutaraldehyde and the periodate methods (E. Ishikawa et al. (1984) J. Immunoassay 4, 209–327).

Radioimmunoassays and enzyme immunoassays are employed to an increasing extent for the diagnosis of, for example, hepatitis B virus infections, and it has been possible in recent years to improve decisively both the sensitivity and specificity of detecting a hepatitis B virus infection. After an infection with hepatitis B virus, the viral antigens and the antibodies corresponding to them appear in the serum of the affected person in a particular sequence which is related to the replication of the virus and the reaction of the immune system of the host. Of the different diagnostic and serologic markers, determination of the hepatitis Bsurface antigen (HBsAg) is of paramount importance both for avoiding transfer of infectious blood or plasma in transfusion medicine and for differential diagnosis. Since it must be assumed that even the smallest quantities of virus are infectious, the highest possible demands are placed on the detection limit of a test for HBsAg.

Enzyme immunoassays can be constructed according to different principles known to the person skilled in the art (e.g. sandwich principle, competitive, indirect, etc.). The sandwich principle is generally employed for detecting HBsAg, with a solid phase coated with anti-HBs antibodies being incubated with the sample under investigation. If HBsAg is present in the sample being investigated, it will bind to the immobilized antibodies. A ternary complex (sandwich) is formed using a second antibody which is coupled to a labelling enzyme. After that, the unbound reactants are separated off by means of several washing steps.

After adding a substrate/chromogen mixture, the formation of the sandwich complex which has arisen is demonstrated by a color reaction which is detected photometrically. Enzyme immunoassays for HBsAg according to the above-described principle are available commercially and have also been described in detail in the specialist literature.

The enzyme immunoassays for detecting, for example, HBsAg, which are described in the specialist literature and which are commercially available, are distinguished by high sensitivity and specificity. In spite of the good specificity of the processes for detecting HBsAg, sera are known whose donors are demonstrably not hepatitis B-positive but which nevertheless yield falsely-positive results ("problem sera"). In general, the falsely-positive and positive samples can be differentiated by repeating the HBsAg detection test or by using diverse confirmatory tests. For the user, however, this is associated with additional expenditure of time and money. It is necessary, therefore, to endeavour to keep the danger of falsely-positive results as low as possible right from the stage of the actual initial test.

EP 0 209 155 discloses an enzyme immunoassay for determining thyroxine in which a periodate oxidation of the labelling enzyme leads to derivatives which yield correct results with "problem sera" as well. In this case, owing to the competitive principle, falsely-lowered extinction values, and consequently falsely-raised analytical values, are measured. An improvement of the specificity was achieved by, prior to or after conjugation with the immunological ligand, treating the labelling enzyme, which contains a carbohydrate moiety, with periodic acid or an alkali metal salt of the latter in aqueous medium and reducing the oxidation product obtained with sodium borohydride. The actual coupling reaction in this case is effected using a heterobifunctional conjugation method which acts on the protein moieties of the labelling enzyme and the immunological ligand.

The object of the present invention was therefore to remove this disadvantage in the specificity and, with the aid of an improved technique, to produce conjugates which yield correct results in the case of problem sera as well.

Surprisingly, it turned out that, when the conjugation technique according to the invention was used, it was possible not only to eliminate disadvantages in the specificity but also to improve the sensitivity of the HBsAg detection.

The invention therefore relates to a process for preparing a conjugate consisting of a specific binding partner and a carbohydrate-containing protein, which process includes the following steps:

a) oxidizing the carbohydrate-containing protein with periodic acid or with a corresponding alkali metal salt in buffered solution, b) introducing additional amino groups into the oxidized protein by reaction with a diamine and reductive stabilization, and subsequently c) coupling the specific binding partner and the activated protein via a heterobifunctional reagent.

In this context, a process as claimed in claim 1 is preferred, in which process the carbohydrate moiety of the protein amounts to 4 to 80% by weight.

In this context, the oxidation is preferably effected at a pH of 4 to 8.

The reaction with the diamine and reductive stabilization are preferably effected at a pH of 7 to 9.5.

Very preferably, the carbohydrate-rich protein is an enzyme, particularly preferably horseradish peroxidase.

Such a process is also preferred in which a diamine of the formula $H_2N-(X)_n-NH_2$ is used for the reaction in step b), where X is preferably an aliphatic combining unit of the formula $-(CH_2)_n-$ or $-(CH_2)_n-O-(CH_2)_n-$ and n is a number from 2 to 12; very preferably diaminohexane is used as the diamine.

The invention also relates to a conjugate which can be prepared by the process according to the invention.

The invention furthermore relates to the use of such a conjugate in immunological detection processes, in particular in an enzyme immunoassay, preferably in a one-step enzyme immunoassay.

The conjugation technique according to the invention is distinguished by the fact that the actual coupling between the labelling enzyme and the immunologically active ligand does not take place via the protein moiety of the labelling enzyme but instead via the oxidized carbohydrate moieties and subsequently introduced amino groups of the labelling enzyme.

In order to improve the specificity and sensitivity of the HBsAg detection, a process for preparing conjugates was discovered, which process comprises, on the one hand, a carbohydrate-containing labelling enzyme, such as, for example, horseradish peroxidase (POD), glucose oxidase (GOD), alkaline phosphatase (AP) and fructosidase (invertase), as the coupling component, and, on the other, immunologically active binding partners, such as, for example, polyclonal and monoclonal antibodies and their derivatives and fragments; as well as antigens and haptens.

In the conjugation technique according to the invention, the amino groups of the labelling enzyme are first blocked with 1-fluoro-2,4-dinitrobenzene and the carbohydrate-containing side chains of the labelling enzyme are then oxidized with sodium periodate. In this connection, the amino groups do not necessarily need to be blocked, and other substances than 1-fluoro-2,4-dinitrobenzene can also be used. The aldehyde groups produced as a result of the periodate oxidation react with the amino groups of an added diamine of the formula $H_2N-(X)_n-NH_2$, resulting in the formation of Schiff's bases which can be reductively stabilized by treating with sodium borohydride.

The amino groups introduced in this way are reacted with iminothiolane, with the free sulfhydryl groups which are thereby produced then reacting via a bridge-forming heterobifunctional reagent (such as, for example, N-maleimidobutyryloxysuccinimide, GMBS) with the free amino groups of the respective immunological binding partner.

It is known per se to the person skilled in the art that, in the reactions, the temperatures are to be suited to the known conditions for maintaining the enzyme activity of the carbohydrate-containing labelling enzyme, such as, for example, horseradish peroxidase.

In this context, the oxidation is preferably effected at pH values between 4.0 and 8.0—preferably at pH 7.0 in buffered solution. The reductive stabilization of the Schiff's bases which are formed is preferably carried out at pH values between 7.0 and 9.5—preferably at pH 8.5.

Because the temperature stability of POD is good, the abovementioned reactions can be effected preferably at temperatures between 0° C. and +37° C., preferentially, however, at room temperature.

The example below is intended to illustrate the invention without in any way limiting it. This is valid, in particular, for other carbohydrate-containing labelling enzymes besides POD, such as, for example, GOD, AP and invertase, which appear to be suitable within the scope of the invention.

EXAMPLE a) Preparation of Conjugate I

The antibody is reacted with a heterobifunction reagent (Tanimori et al. (1983) J. Imm. Meth..62, 123–131), and then incubated with SH-activated peroxidase (King et al. (1978) Biochemistry 17, 1499–1506) and subsequently purified by gel chromatography.

b) Preparation of Conjugate II

The labelling enzyme, peroxidase, is reacted with 1-fluoro-2,4-dinitrobenzene, and then oxidized with periodate. The aldehyde groups thus obtained are coupled to the amino groups of the antibody. The Schiiff's bases which arise are then reduced with sodium brohydride (P. Tijssen (1985) Laboratory Techniques in Biochemistry and Molecular Biology, 223–241). The reaction products are subsequently purified by gel chromatography from the free peroxidase and the free antibody.

c) Preparation of Conjugate III 20 mg of peroxidase are dissolved in 20 mM sodium phosphate buffer (pH 7.0), and 0.4 ml of 1-fluoro-2,4-dinitrobenzene solution (10 µl of 1-fluoro-2,4-dinitrobenzene +1.93 ml of ethanol) is added. The mixture is incubated at room temperature for 1 h, 0.6 ml of a 0.25M sodium periodate solution is then added, and incubation is continued at room temperature for a further 30 min with the exclusion of light.

Excess reagent is subsequently removed by gel chromatography, with the column previously having been equilibrated with 20 mM sodium phosphate buffer (pH 7.0). The concentration of the peroxidase which has been preactivated in this way is determined at 403 nm ($\epsilon=2.275\ g^{-1}.L.cm^{-1}$).

2.5 ml of peroxidase (7.5 mg) are diluted with 7.0 ml of 0.2M sodium hydrogen carbonate/150 mM NaCl (pH 8.5), and then 1.0 ml of diaminohexane solution (5.8 mg/ml in 0.2M sodium carbonate/150 mM NaCl pH 8.5) is added, and the mixture is incubated at room temperature for 2 h with the exclusion of light. Subsequently, 0.9 ml of a sodium borohydride solution (5 mg/ml) is added to this solution, which is then left to stand for 2 h in an open vessel. 1.2 ml of a 1M ethanolamine/HCl solution (pH 8.0) are added to the reaction mixture, which is incubated at 4° C. overnight. On the following day, the peroxidase solution is concentrated and re-buffered in 25 mM sodium tetraborate. The peroxidase concentration should be 1.5–2.0 mg/ml. 83 µl of a 1M iminothiolane solution (dissolved in methanol) are added to 8 mg of peroxidase solution and the mixture is incubated at room temperature for 2 h, and excess reagent is subsequently removed by gel chromatography using 0.1M sodium phosphate buffer (pH 6.0), and the concentration determined at 403 nm. 4 mg of antibody (2 mg/ml of solution in 0.1M lithium borate buffer, pH 8.0) are mixed with 70 µl of GMBS solution (3 mg/ml in dioxane), and then incubated at room temperature for 1 h and subsequently re-buffered in 0.1M sodium phosphate buffer (pH 6.0).

1.2 ml of solution of activated peroxidase (4.3 mg) are added to 2.7 ml of activated antibody (3.25 mg), and the mixture is then incubated at room temperature for 2 h, and the reaction subsequently stopped with 0.5 ml of an 0.1M N-ethylmaleimide solution.

d) HBsAg Enzyme Immunoassay

A typical enzyme immunoassay for detecting HBsAg, such as, for example, Enzygnost HBsAg monoclonalII is based on the one-step sandwich principle. The HBsAg contained in the investigated sample (100 µl) reacts simultaneously with the polyclonal anti-HBs antibody, which is fixed in the well of the microtitration plate, and with the monoclonal, peroxidase-conjugated anti-HBs antibody (anti-HBs/POD conjugate). The incubation time is 90 min at +37° C. After removing the unbound reactants by sucking off and by washing four times, the quantity of the bound conjugate is determined by adding 100 µl of substrate/chromogen solution (room temperature, 30 min and protected from light). The enzymic conversion of the chromogen, tetramethylbenzidine dihydrochloride, is interrupted by adding 100 µl of 0.5N sulfuric acid, and the extinction at 450 nm is determined photometrically. The extinction which is recorded is proportional to the concentration of HBsAg present in the sample.

Using the conjugates according to the invention in the enzyme immunoassay, it was possible to demonstrate not only that a decisive improvement can be achieved in the sensitivity of the HBsAg detection, but also that falsely-positive signals no longer occurred in problem sera. Table I shows the results of an HBsAg enzyme immunodetermination using conjugates which were obtained a) by way of a heterobifunctional reagent (= conjugate I)

b) by the conventional Nakane method (=conjugate II)

c) by the method according to the invention (=conjugate III).

The comparison is of a negative control and of HBsAg samples which were calibrated against a standard material obtained from the Paul Ehrlich Institute (Frankfurt, FRG).

The sensitivity, which was calculated by linear regression and by taking into consideration a threshold value of 50 mE, is also given.

TABLE I

Sensitivity comparison for conjugates I–III

| Sample | Conjugate I | Conjugate II | Conjugate III |
|---|---|---|---|
| neg. contr. | 37 mE | 64 mE | 44 mE |
| 0.05 U/ml | 69 mE | 56 mE | 93 mE |
| 0.10 U/ml | 82 mE | 74 mE | 153 mE |
| 0.20 U/ml | 133 mE | 114 mE | 276 mE |
| 0.50 U/ml | 301 mE | 241 mE | 639 mE |
| 1.00 U/ml | 584 mE | 525 mE | 1247 mE |
| 2.00 U/ml | 1257 mE | 1051 mE | 2517 mE |
| Sensitivity | 0.12 U/ml | 0.20 U/ml | 0.06 U/ml |

Table II shows the results of an HBsAg enzyme immunodetermination using conjugates which were obtained a) via a heterobifunctional reagent (= conjugate I)

b) by the conventional Nakane method (=conjugate II)

c) by the method according to the invention (=conjugate III).

The comparison is of negative control, cut-off value, three normal sera (NS 1-NS 3) and ten "problem sera" (PS 1-PS 10). The threshold value was set at 50 mE, with the cut-off value being calculated as the sum of the threshold value and the negative control.

TABLE II

Specificity comparison for conjugates I–III

| Sample | Conjugate I | Conjugate II | Conjugate III |
|---|---|---|---|
| neg. contr. | 16 mE | 52 mE | 60 mE |
| cut-off | 66 mE | 102 mE | 110 mE |
| NS 1 | 20 mE | 73 mE | 55 mE |
| NS 2 | 25 mE | 77 mE | 60 mE |
| NS 3 | 28 mE | 80 mE | 66 mE |
| PS 1 | 105 mE | 73 mE | 74 mE |
| PS 2 | 248 mE | 41 mE | 39 mE |
| PS 3 | 455 mE | 27 mE | 42 mE |
| PS 4 | 364 mE | 87 mE | 68 mE |
| PS 5 | 251 mE | 90 mE | 56 mE |
| PS 6 | 569 mE | 31 mE | 27 mE |
| PS 7 | 3283 mE | 76 mE | 56 mE |
| PS 8 | 14 mE | 106 mE | 85 mE |
| PS 9 | 9 mE | 105 mE | 78 mE |
| PS 10 | 29 mE | 139 mE | 81 mE |

We claim:

1. A process for preparing a conjugate consisting of a specific binding partner and a carbohydrate-containing protein, comprising the steps of:

(a) oxidizing the carbohydrate-containing protein with periodic acid or with a corresponding alkali metal salt in a buffered solution, (b) introducing additional amino groups into the oxidized protein by reaction with a diamine and reductive stabilization, (c) reacting the amino groups introduced in step (b) with iminothiolane which results in the formation of sulfhydryl groups, and subsequently (d) coupling the specific binding partner and the protein activated in steps (a)–(c) via a heterobifunctional reagent.

2. The process as claimed in claim 1, wherein the carbohydrate moiety of the protein is 4 to 80% by weight.

3. The process as claimed in claim 1, wherein the oxidation is effected at a pH of 4 to 8.

4. The process as claimed in claim 1, wherein the reaction with the diamine, and reductive stabilization, are effected at a pH of 7 to 9.5.

5. The process as claimed in claim 1, wherein the carbohydrate-rich protein is an enzyme.

6. The process as claimed in claim 5, wherein the enzyme is horseradish peroxidase.

7. The process as claimed in claim 1, wherein a diamine of the formula $H_2N-(X)_n-NH_2$ is used for the reaction in step b) and wherein X is an aliphatic combining unit of the formula $-(CH_2)_n-$ or $-(CH_2)_n-O-(CH_2)_n-$ and n is a number from 2 to 12.

8. The process as claimed in claim 7, wherein X is an aliphatic combining unit of the formula $-(CH_2)_n-$.

9. The processas claimed in claim 7, wherein diaminohexane is used as the diamine.

10. A conjugate, which is prepared by thee process as claimed in claim 1.

11. A method for using a conjugate as claimed in claim 10 in immunological detection processes, comprising the steps of:
    (a) coating a solid phase with antibodies against the antigen being investigated so as to immobilize said antibodies,
    (b) incubating the immobilized antibodies with a sample containing the antigens,
    (c) incubating the immobilized antibody/antigen sample with a second antibody which is coupled to a labelling enzyme,
    (d) separating the unbound reactants by washing and suction,
    (e) adding a substrate/chromogen solution,
    (f) interrupting the enzymatic conversion of the chromogen to form a sandwich complex which is detected photometrically.

12. The method as claimed in claim 11 wherein the immunological detection process is an enzyme immunoassay.

13. The method as claimed in claim 12, wherein the enzyme immunoassay is a one-step enzyme immunoassay.

14. The process as claimed in claim 1, wherein diamine of the formula $H_2N-CH_2-NH_2$ is used for the reaction in step b).

15. The process according to claim 1, wherein the specific binding partner is an antibody against hepatitis B surface antigan.

16. The method according to claim 12, wherein the enzyme immunoassay detects hepatitis B surface antigen.

17. The method according to claim 13, wherein the one-step enzyme immunoassay detects hepatitis B surface antigen.

* * * * *